(12) United States Patent
Taneda

(10) Patent No.: US 10,121,643 B2
(45) Date of Patent: Nov. 6, 2018

(54) CHROMATOGRAPHY/MASS SPECTROMETRY DATA PROCESSING DEVICE

(71) Applicant: SHIMADZU CORPORATION, Kyoto-shi, Kyoto (JP)

(72) Inventor: Katsuyuki Taneda, Kyoto (JP)

(73) Assignee: SHIMADZU CORPORATION, Kyoto-shi, Kyoto (JP)

( * ) Notice: Subject to any disclaimer, the term of this patent is extended or adjusted under 35 U.S.C. 154(b) by 804 days.

(21) Appl. No.: 14/339,607

(22) Filed: Jul. 24, 2014

(65) Prior Publication Data

US 2016/0025691 A1 Jan. 28, 2016

(51) Int. Cl.

| | | |
|---|---|---|
| *G01N 30/00* | (2006.01) | |
| *H01J 49/00* | (2006.01) | |
| *G01N 30/72* | (2006.01) | |
| *G06F 19/00* | (2018.01) | |
| *G01N 30/86* | (2006.01) | |
| *H01J 49/26* | (2006.01) | |

(52) U.S. Cl.
CPC .......... *H01J 49/0036* (2013.01); *G01N 30/72* (2013.01); *G01N 30/8637* (2013.01); *G06F 19/703* (2013.01); *G01N 30/7206* (2013.01); *G01N 30/7233* (2013.01); *H01J 49/0027* (2013.01); *H01J 49/0095* (2013.01); *H01J 49/26* (2013.01)

(58) Field of Classification Search
CPC . G01N 30/72; G01N 30/7206; H01J 49/0036; H01J 49/004
See application file for complete search history.

(56) References Cited

U.S. PATENT DOCUMENTS

| | | | | |
|---|---|---|---|---|
| 4,008,388 A | * | 2/1977 | McLafferty | ........... G06F 19/703 250/281 |
| 2014/0183353 A1 | * | 7/2014 | Shimada | ............. H01J 49/0036 250/282 |

FOREIGN PATENT DOCUMENTS

JP 2010-054406 A 3/2010

* cited by examiner

*Primary Examiner* — Mischita Henson
*Assistant Examiner* — Christine Liao
(74) *Attorney, Agent, or Firm* — Sughrue Mion, PLLC

(57) ABSTRACT

Using the intensity ratio of peaks on a standard mass spectrum of the target compound and peaks with the same m/z on the measured mass spectrum near the retention time of said compound, a scale factor waveform close to the chromatogram shape based on the target compound alone is computed, and m/z candidates for quantitation are extracted based on the correlation between the measured mass chromatogram of the target compound and the scale factor waveform. Furthermore, an intensity ratio is determined with reference to the m/z peaks showing the greatest scale factor on the measured mass spectrum at the measurement time point showing the greatest scale factor in the scale factor waveform, and m/z candidates for quantitation/confirmation are narrowed down based on whether they fall within an allowable range based on peak intensity ratio on the standard mass spectrum.

11 Claims, 5 Drawing Sheets

CHROMATOGRAPHY/MASS SPECTROMETRY DATA PROCESSING DEVICE

TECHNICAL FIELD

The present invention relates to a chromatography/mass spectrometry data processing device which quantitates a target compound in a sample based on data acquired with a chromatograph/mass spectrometer such as a gas chromatograph/mass spectrometer (GC/MS) or liquid chromatograph/mass spectrometer (LC/MS); more specifically, the present invention relates to a chromatography/mass spectrometry data processing device suitable for quantitating a target compound in a sample containing many impurity components.

BACKGROUND ART

In a chromatograph/mass spectrometer such as GC/MS or LC/MS, the various components contained in a sample are separated in the time direction by a chromatograph, and the ions derived from the separated components are detected. To perform quantitative analysis of a target compound in a sample by GC/MS or LC/MS, generally, a mass chromatogram (also called an ion extraction chromatogram) at a mass-to-charge ratio corresponding to the target compound is prepared, and the area value of chromatogram peaks appearing near the retention time of the target compound in the mass chromatogram is determined. Those area values are then compared to a calibration curve (a regression curve associating concentration with area) prepared in advance, and the concentration i.e. quantitative value of the target compound is computed. Therefore, to increase the precision of quantitative analysis, it is necessary to prevent overlap of components other than the target compound, i.e. of impurity components, with the chromatogram peak on the mass chromatogram.

Thus, conventionally, for example, physical or chemical pretreatment would be performed on a sample to remove impurity components prior to analysis to the extent possible, or the separation conditions of the chromatograph would designed so as to avoid overlap between the target compound and impurity components to the extent possible. However, in cases where there are numerous impurity components or where unknown impurity components are mixed in, by the techniques described above, it is difficult to completely avoid overlap with impurity components that would hinder quantitative analysis.

As another technique for increasing the precision of quantitation of a target compound, changing the mass-to-charge ratio of the mass chromatogram for performing quantitative computations may be considered. Namely, there are usually not one but multiple peaks (mass spectrum peaks) observed on the mass spectrum for a given target compound. It is unlikely that the same effect of overlap of impurity components will exist for all the mass-to-charge ratios at which those multiple peaks appear, and since there will be mass-to-charge ratios with little or no overlap of impurity components, by suitably specifying the mass-to-charge ratio for generating the mass chromatogram for quantitative analysis (hereinafter referred to as "quantitation mass-to-charge ratio"), it is possible to reduce the effect of impurity components and improve quantitative characteristics.

Furthermore, if impurity components with a peak appearing at the aforementioned quantitation mass-to-charge ratio on the mass spectrum are present, it is difficult to distinguish the target compound from the impurity components based on the quantitation mass-to-charge ratio alone. Thus, generally, a confirmation mass-to-charge ratio is specified separately from the quantitation mass-to-charge ratio, the relative ratio (hereinafter referred to as "confirmation ion ratio") between the peak intensity for the confirmation mass-to-charge ratio and the peak intensity for the quantitation mass-to-charge ratio is determined on a mass spectrum representative of the peaks appearing on the mass chromatogram at the quantitation mass-to-charge ratio, and if the confirmation ion ratio is within a predetermined range, the peak of that mass chromatogram is judged to be derived from the target compound. For this purpose, the confirmation mass-to-charge ratio is also selected to be a mass-to-charge ratio with as little overlap as possible with impurity components other than the target compound.

With a conventional GC/MS or LC/MS data processing device, the analyst can determine and set the aforementioned quantitation mass-to-charge ratio and confirmation mass-to-charge ratio as one of the measurement parameters. To this end, the analyst visually checks the standard mass spectrum of a known target compound, and selects, through trial and error, from among the mass-to-charge ratios for which a clear peak can be observed on the mass spectrum, a mass-to-charge ratio such that the shape of chromatogram peak on the mass chromatogram is a shape close to normal distribution.

However, even when the target compound is the same, if the other impurity components contained in the sample are different, the quantitation mass-to-charge ratio and confirmation mass-to-charge ratio will need to be modified in some cases, so particularly in cases where there are many target compound types, the work of determining the quantitation mass-to-charge ratio and confirmation mass-to-charge ratio is very laborious and takes much time. Furthermore, in cases where the target compound and impurity components overlap completely, operations which depend on the analyst's experience and skill becomes necessary, e.g. comparing mass chromatograms at multiple mass-to-charge ratios and finding a mass-to-charge ratio with the least influence of impurity components, so it is possible that differences in analyst experience and skill will be reflected in the analysis results.

In Patent Literature 1 and Non-patent Literature 1, the present applicant proposed an algorithm (hereinafter referred to as "time series minimum point plotting method") for accurately estimating the shape of the chromatogram peaks of a target compound even when complete component separation with a chromatograph is not possible and the target compound is mixed with unknown impurity components. The basic idea of this method is as follows.

When a target compound is present in a sample, a peak derived from that target compound will appear near the retention time of the target compound on a mass chromatogram at a specific mass-to-charge ratio. If other components are not present around this retention time, it should be possible to represent the mass spectrum at various times near the retention time of the target compound using a constant scaling factor of the standard mass spectrum of the target compound. By contrast, if impurity components are present near the retention time of the target compound, the peak intensity of the measured mass spectrum will increase on account of the impurity components. However, normally, since many peaks are present in the standard mass spectrum of the target compound, it is unlikely that impurity components will affect all of the many peaks in the measured mass spectrum at a given time. Therefore, it can be surmised that, in the mass spectrum for each time, a peak derived from the target compound and not affected by impurity components will appear at least at some of the mass-to-charge ratios. Namely, by determining the intensity ratio of peaks at a mass-to-charge ratio not affected by impurity components at various times near the retention time of the target compound, it is possible to estimate the chromatogram peak shape of the target compound from which the influence of impurity components has been eliminated.

In Patent Literature 1 and Non-patent Literature 1, the similarity between chromatogram peaks estimated as described above and calculated chromatogram peaks is evaluated to determine if the target compound is contained in a sample. In the case of such compound identification, even if the estimated chromatogram peaks contain some impurity components, the identification precision will rarely be reduced significantly. By contrast, when performing quantitation of a known compound, if impurity components overlap the chromatogram peak serving as the basis for the quantitation, that overlap will directly lead to a decrease in quantitation precision. Therefore, for high precision quantitative analysis, a time series minimum point plotting method as described above is inadequate.

PRIOR ART LITERATURES

Patent Literatures (Patent literature 1) Japanese Unexamined Patent Application Publication 2010-054406

Non-Patent Literatures (Non-patent literature 1) OZAWA and one other. "Component identification for residual agrochemicals in food products based on peak estimation using a time series minimum point plotting method", Shimadzu Review Editorial Department, Shimadzu Review, Vol. 65, Nos. 1 & 2, published Sep. 30, 2008.

The present invention was made to resolve the problem described above, its purpose being to provide a chromatography/mass spectrometry data processing device capable of automatically and reliably extracting a mass-to-charge ratio with little or no influence of overlap of impurity components on a mass chromatogram in order to ensure a high quantitation precision when quantitating a target compound in a sample wherein many impurity components are mixed together.

SUMMARY OF THE INVENTION

The present invention, made to resolve the aforementioned problem, is a chromatography/mass spectrometry data processing device which analyzes and processes data having, as dimensions, mass-to-charge ratio, time and signal intensity obtained by repeatedly executing mass analysis across a predetermined mass-to-charge ratio range after separating the components in a sample in the time direction with a chromatograph, the chromatography/mass spectrometry data processing device being characterized in that it comprises:

a) a chromatogram peak shape estimation unit which, using the intensity ratio [of] the intensity of a peak on a standard mass spectrum of a target compound which is the object of analysis and the intensity of peaks having the same mass-to-charge ratio on the measured mass spectrum at various measurement time points near the retention time of said target compound, estimates the shape of chromatogram peaks due to said target compound from which the influence of overlap of impurity components has been eliminated;

b) a chromatogram peak correlation determination unit which determines the correlation between the shape of the chromatogram peaks obtained by said chromatogram peak shape estimation unit and the peaks of said target compound on the measured mass chromatogram obtained at each charge-mass ratio;

c) a mass spectrum peak purity determination unit which determines the mass spectrum peaks originating solely from the target compound based on the intensity ratio of multiple peaks on the standard mass spectrum of said target compound and the intensity ratio of multiple peaks having the same mass-to-charge ratio on the measured mass spectrum of the target compound at a specific measurement time point; and d) a mass-to-charge ratio derivation unit which, using the determination results of said chromatogram peak correlation determination unit and the determination results of said mass spectrum peak purity determination unit, derives a mass-to-charge ratio as a confirmation mass-to-charge ratio and/or quantitation mass-to-charge ratio used for quantitating said target compound.

The target compound is known. Therefore, by measuring standard samples containing the target compound, it is possible to determine in advance the standard mass spectrum and retention time of the target compound. Furthermore, for example, such information on various compounds may be stored in advance in a database, so that when the target compound is specified, the corresponding standard mass spectrum and retention time can be obtained. Since retention time depends on analysis conditions such as flow velocity of the mobile phase of the chromatograph, a retention indicator not dependent on such analysis conditions may be stored in the database, and the retention time may be computed based on the retention indicator.

If impurity components are not present around the retention time of the target compound separated in the time direction by a chromatograph such as a GC or LC, in other words, if only the chromatogram peak of the target compound alone is present, then the mass spectrum at each measurement time point near the retention time of the target compound can be represented using a constant scaling factor of the standard mass spectrum of the target compound. By contrast, when impurity components are present before or after the retention time of the target compound, the peak intensity of the measured mass spectrum should increase on account of the impurity components. However, since multiple peaks generally appear on the standard mass spectrum of the target compound, as described above, it is unlikely that the impurity components will affect all the peaks in the measured mass spectrum at a given measurement time point. Thus, it can be assumed that peaks originating purely from the target compound which are unaffected by impurity components will appear for at least some of the mass-to-charge ratios on the mass spectrum at each measurement time point. Therefore, by finding the ratio between the intensity of a peak at a mass-to-charge ratio not affected by impurity components at various measurement time points near the retention time of the target compound, and the peak intensity for the same mass-to-charge ratio on the standard spectrum, it is possible to estimate the chromatogram peak shape of the target compound unaffected by impurity components.

If impurity components overlap a peak derived from the target compound on the measured mass spectrum at a given measurement time point, the intensity of that peak should be greater than when there are no impurity components. Thus, as one mode of the present invention, a configuration can be employed wherein said chromatogram peak shape estimation unit determines the intensity ratio Ps/Pr (where Ps: peak intensity on measured mass spectrum; Pr: peak intensity on standard mass spectrum) of peaks having the same mass-to-charge ratio on the measured mass spectrum at a given measurement time point for the mass-to-charge ratio of all or some of the peaks on the standard mass spectrum of said target compound, takes the smallest of the multiple intensity ratios Ps/Pr as the scale factor at that measurement time point, and arranges the scale factors determined at each measurement time point in time series order to estimate the shape of the chromatogram peak of said target compound. Here, "some of the peaks" refers, for example, to peaks whereof the intensity is at or above a predetermined value, or a predetermined number of peaks selected in descending order of intensity, or peaks selected based on predetermined criteria.

Furthermore, as another mode of the present invention, a configuration may be employed wherein, when the intensity of all or some of the peaks on the standard mass spectrum of said target compound is multiplied by a constant scaling factor and compared to the intensity of the peak having the same mass-to-charge ratio on the measured mass spectrum at a given measurement time point, said chromatogram peak shape estimation unit determines a constant scale factor such that the former intensity does not exceed the latter and arranges the scale factors determined at each measurement time point in time series order to estimate the shape of the chromatogram peaks of said target compound. In this case, the scaling factor at a given measurement time point is determined based on peaks with little influence of impurity components in the measured mass spectrum, thereby making it possible to estimate chromatogram peaks of the target compound from which the influence of impurity components has been eliminated, just as in the mode described previously.

In chromatography/mass spectrometry, tailing may occur on chromatogram peaks of the target compound due to factors such as measurement environment and measurement parameters. Furthermore, chromatogram peaks due to isomers may approach the chromatogram peak of the target compound, so even if a standard sample is measured, the chromatogram peaks will not always be normal distribution-like. By contrast, with the chromatogram peak shape estimation unit, a scale factor waveform of the target compound is generated based on a standard spectrum not affected by impurity components, and the shape thereof is similar to shapes containing tailing and isomers, so it is easy to judge if the mass chromatogram at each mass-to-charge ratio is a pure shape or not.

It should be noted that the target compound chromatogram peak estimation method employed by the aforesaid chromatogram peak shape estimation unit corresponding to the time series minimum point plotting method described above.

In the chromatography/mass spectrometry data processing device according to the present invention, the chromatogram peak correlation determination unit computes the correlation coefficient of the shapes of the chromatogram peaks estimated by the aforementioned technique and the peaks of the target compound on the measured mass chromatogram obtained for each mass-to-charge ratio, and, for example, compares that correlation coefficient to a predetermined threshold value to extract a mass-to-charge ratio for which a high correlation is obtained.

Furthermore, the mass spectrum peak purity determination unit, separately from the determination by the aforementioned chromatogram peak correlation determination unit, based on the intensity ratio of multiple peaks on the standard mass spectrum of the target compound and the intensity ratio of multiple peaks having the same mass-to-charge ratio on the measured mass spectrum of the target compound at each measurement time point, determines the mass spectrum peaks derived solely from the target compound.

More specifically, the mass spectrum peak purity determination unit can be configured such that it determines the reference measurement time point and reference mass-to-charge ratio which give the peak top of the chromatogram peak obtained by the chromatogram peak shape estimation unit, and, taking as reference the ratio of the peak intensity for the reference mass-to-charge ratio on the standard mass spectrum of the target compound to the peak intensity at an arbitrary mass-to-charge ratio, determines if the ratio of peak intensity for the reference mass-to-charge ratio on the measured mass spectrum at said reference measurement time point to the peak intensity at said arbitrary mass-to-charge ratio falls within a predetermined range in relation to said reference, and thereby judges if the peak for the arbitrary mass-to-charge ratio is a mass spectrum peak originating solely from said target compound. As a result, it becomes possible to eliminate from the objects of selection those mass-to-charge ratios where impurity components overlap near the peak top of the chromatogram, which has the greatest influence on quantitation precision.

Furthermore, the mass-to-charge ratio derivation unit, using the determination results of the chromatogram peak correlation determination unit and the determination results of the mass spectrum peak purity determination unit, extracts a mass-to-charge ratio for which the influence of impurity components is judged to be small in both the determination results, and determines this to be a mass-to-charge ratio suitable as a quantitation mass-to-charge ratio and/or confirmation mass-to-charge ratio. One or multiple mass-to-charge ratios determined in this manner may be displayed for example on a display screen, and when a quantitation mass-to-charge ratio is selected therefrom in accordance with the analyst's instructions, quantitation of the target compound is performed using the peaks appearing in the mass chromatogram at that quantitation mass-to-charge ratio. Furthermore, when a confirmation mass-to-charge ratio is selected in accordance with the analyst's instructions, for example, based on a confirmation ion ratio determined from the intensity of the peaks at the confirmation mass-to-charge ratio and quantitation mass-to-charge ratio on a mass spectrum representative of the aforementioned mass chromatogram peaks, it is determined if the given mass chromatogram peak is derived from the target compound or not. Alternatively, quantitation of the target compound may be performed automatically using peaks appearing on the mass chromatogram at one or multiple mass-to-charge ratios determined as described above.

With the chromatography/mass spectrometry data processing device according to the present invention, the determination of similarity of the shape of chromatogram peaks using a standard mass spectrum of the target compound and the determination of purity of peaks on a measured mass spectrum likewise using a standard mass spectrum of the target compound are carried out as a two-stage determination, making it possible to automatically extract a quantitation mass-to-charge ratio having a pure chromatogram peak suitable for quantitation calculations and a confirmation mass-to-charge ratio which allows accurate determination of whether a chromatogram peak is in fact derived from the target compound, even based on data obtained by measuring a standard sample containing impurity components. This simplifies the operation of confirming the quantitation mass-to-charge ratio and confirmation mass-to-charge ratio even if the impurity components contained in the sample change. Furthermore, the effort of investigating in detail the analytical conditions under which overlap between the target compound and impurity components will not occur and of performing pretreatment of samples is reduced.

DETAILED DESCRIPTION OF THE EXEMPLARY EMBODIMENTS

Figure 1:
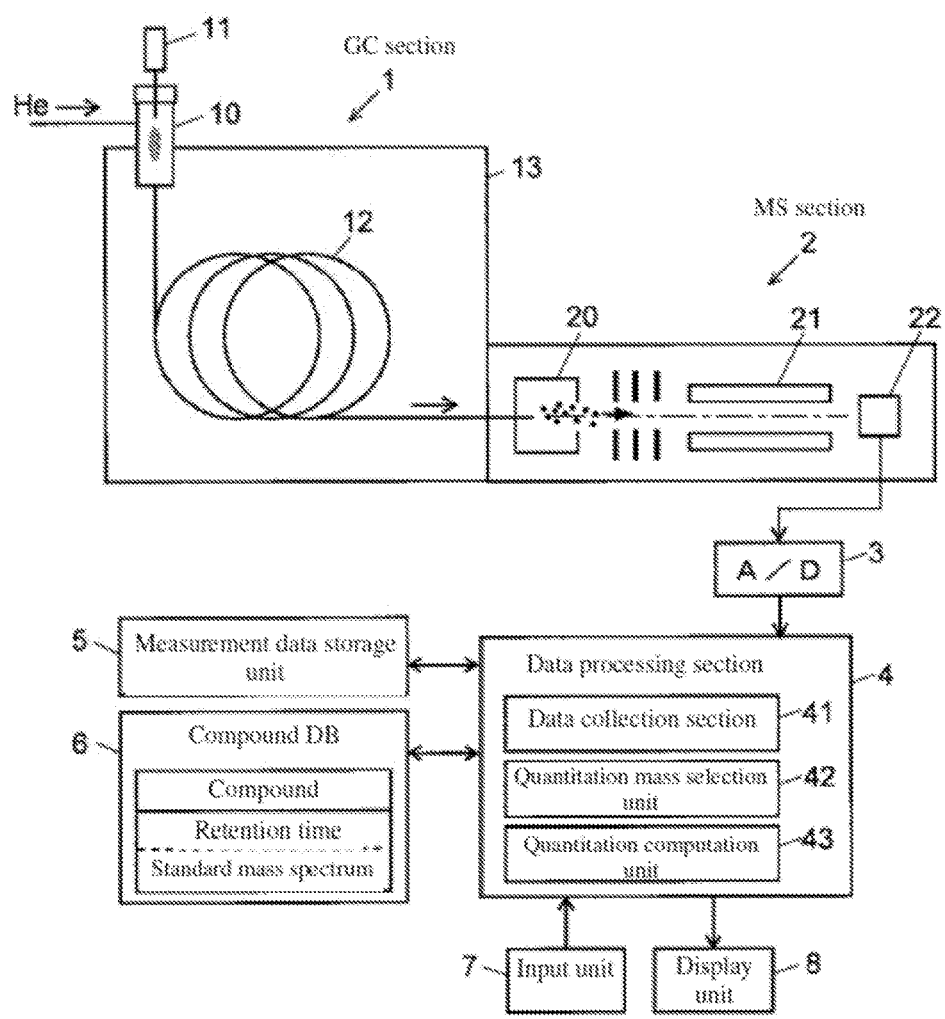
FIG. 1 is an overall diagram of an example of embodiment of a GC/MS to which the chromatography/mass spectrometry data processing device according to the present invention has been applied.

An example of embodiment of a GC/MS to which the chromatography/mass spectrometry data processing device according to the present invention has been applied will be described below with reference to the appended drawings.

The GC/MS of the present example of embodiment comprises a GC section 1 containing a sample gasification chamber 10, injector 11, column 12 and a column oven 13 which encases the column 12; and an MS section 2 containing an ion source 20, quadrupole mass filter 21 and ion detector 22, wherein detection signals produced by the ion detector 22 are converted to digital data in A/D converter 3 and are inputted into data processing unit 4.

In the GC section 1, a carrier gas such as helium is supplied at a constant flow rate through sample gasification chamber 10 to column 12. A small amount of sample is injected through the injector 11 into the sample gasification chamber 10 at a predetermined timing based on instructions of an unillustrated control unit, whereupon the sample is instantaneously gasified and introduced into the column 12 by the carrier gas flow. Then, while passing through the column 12, the temperature of which is regulated by the column oven 13, the various components contained in the sample are separated and flow out of the outlet of the column 12 at different times.

Sample gas flowing out from the column 12 is guided to the ion source 20 in the MS section 2, and the component molecules contained in the sample gas are ionized, for example, through electron ionization or chemical ionization. The generated ions are guided to quadrupole mass filter 21, and only ions having a specific mass-to-charge ratio m/z, in accordance with the voltage applied to the quadrupole mass filter 21, are selectively allowed to pass through and reach the ion detector 22. An unillustrated quadrupole driving unit repeatedly scans the voltage applied to the quadrupole mass filter 21 across a predetermined voltage range, thereby performing mass scanning across a predetermined mass-to-charge ratio range. As a result, in the MS section 2, scanning measurement in a predetermined mass-to-charge ratio range is performed on the sample gas successively introduced over time, and data having the dimensions of mass-to-charge ratio, time and signal intensity is inputted into the data processing unit 4.

Data processing unit 4 comprises, as functional blocks, a data collection unit 41, quantitation mass selection unit 42, quantitation computation unit 43, etc. A measurement data storage unit 5, compound database (DB) 6, input unit 7 and display unit 8 are connected to this data processing unit 4. The compound DB 6 stores basic information such as compound name and structural formula, as well as retention time, standard mass spectrum and the like, for various compounds. It will be noted that the retention time and standard mass spectrum of the target compound may be suitably determined using a standard sample, etc., even if no compound DB has been prepared.

Data collection unit 41 collects data inputted as described above as measurement is performed, and stores it in measurement data storage unit 5. After completion of measurement, upon receiving an instruction to execute data analysis processing (target compound quantitation processing) via input unit 7, the quantitation mass selection unit 42 reads the data constituting the object of analysis from the measurement data storage unit 5, reads information on retention time, etc. pertaining to the target compound from the compound DB 6, and executes the distinctive processing described below to select a quantitation mass-to-charge ratio suitable for quantitation. The quantitation computation unit 43 performs quantitation of the target compound based on the mass chromatogram at the selected mass-to-charge ratio. The quantitative analysis results are displayed on the display unit 8.

The data processing unit 4 and the unillustrated control unit can be embodied using a personal computer, and the functions of the quantitation mass selection unit 42, etc. can be implemented by executing specialized control and processing software installed in advance on the computer.

Figure 2:
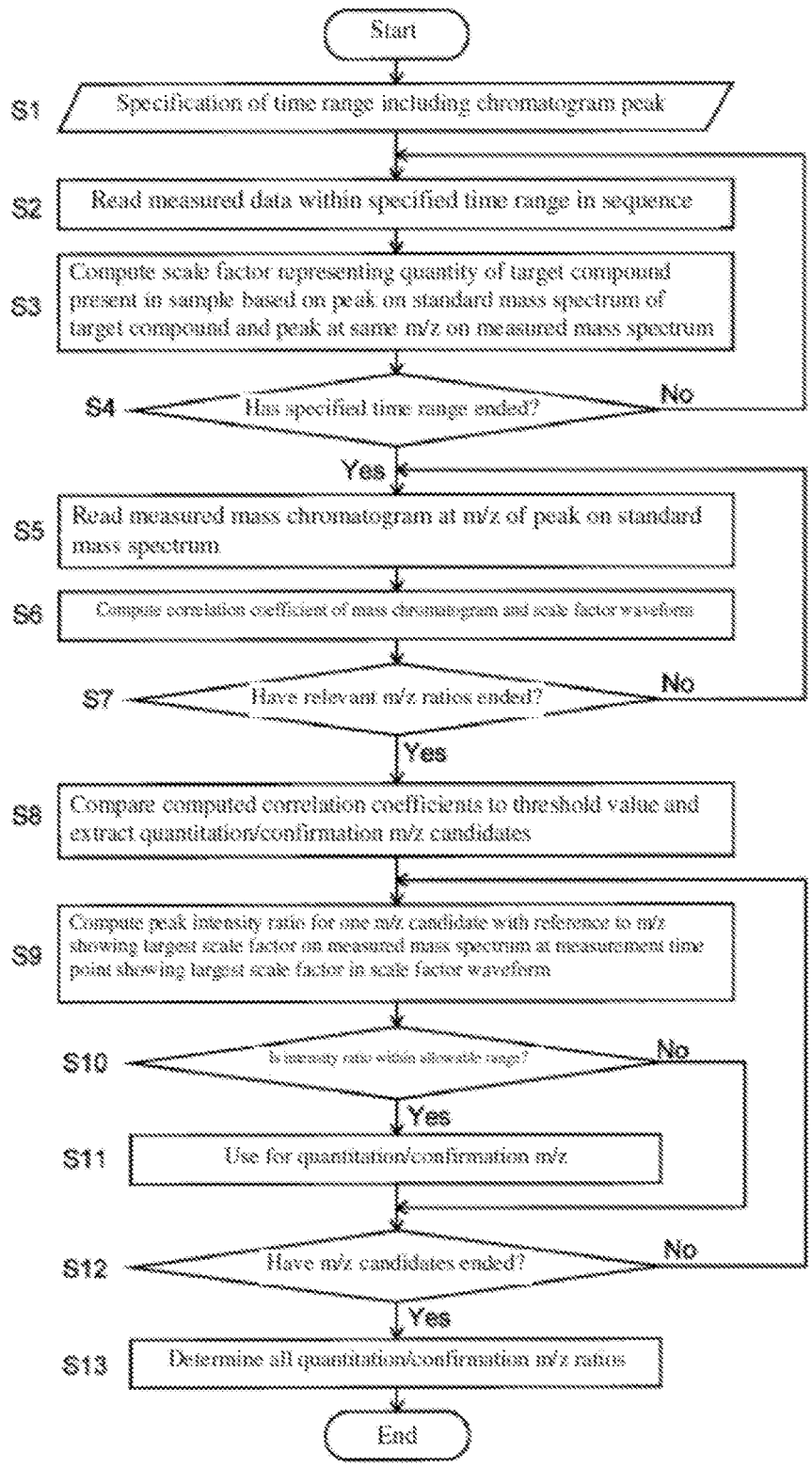
FIG. 2 is a flowchart showing the data processing operation for quantitation mass-to-charge ratio selection performed in the GC/MS of the present example of embodiment.

Even when the separation capacity of the column 12 is high, in simultaneous multicomponent analysis of hundreds of components, which is required in testing for residual agrochemical and the like, it is difficult to fully separate all the components, and the target compound will often be overlapped by other compounds at the outlet of the column 12, as described above. Even in such cases, with the GC/MS of the present example of embodiment, the distinctive processing performed in the data processing unit 4 makes it possible to eliminate the effects of overlap of impurity components to the maximum extent and to achieve high quantitative performance. Next, the distinctive data processing operation performed mainly in the quantitation mass selection unit 42 will be described using FIG. 2. FIG. 2 is a flowchart of this processing operation.

The analyst, by means of input unit 7, specifies the target compound on which quantitation is to be performed, and inputs and sets the processing parameters, such as the time range (Ts, Te) containing the mass chromatogram peaks appearing near the retention time of the target compound (step S1). The time range may also be set automatically.

Upon being instructed to initiate processing execution, the quantitation mass selection unit 42 reads measurement data corresponding to the first measurement time point (mass spectrum acquisition time point) in the specified time range (Ts, Te), i.e. measured mass spectrum data, from the measurement data storage unit 5 (step S2).

Next, the quantitation mass selection unit 42, using the standard mass spectrum of the target compound read from compound DB 6 and the aforementioned measured mass spectrum, calculates a scale factor value representing the quantity of target compound present (step S3). The specific method of calculating the scale factor value is as follows.

It will be assumed that Int_std ($m_i$) is the intensity of the mass spectrum peak at mass-to-charge ratio $m_i$ on the standard mass spectrum of the target compound. Here, i is 1 through n, where n is the total number of mass spectrum peaks on the standard mass spectrum. Furthermore, it will be assumed that Int ($m_i$, t) is the intensity of the mass spectrum peak at mass-to-charge ratio $m_i$ on the measured mass spectrum obtained at measurement time point t. Here, the scale factor value F (t) is computed by the following formula (1).

(Mathematical formula 1)

$$F(t)=\min(Int(m_1,t)/Int\_std(m_1), \ldots, Int(m_n,t)/Int\_std(m_n)) \quad (1)$$

Namely, the scale factor value F (t) is the smallest among the ratios (scale factors) of peak intensity on the measured mass spectrum to peak intensity on the standard mass spectrum determined for the mass-to-charge ratio of all (n) peaks present on the standard mass spectrum of the target compound. The smallest value among the n scaling factors is selected because it is thought that the mass-to-charge ratio at which the scale factor is smallest will have the least influence of impurity components, in other words, the highest purity of the target compound.

Next, it is determined if the processing of steps S2 and S3 has been completed for the entire specified time range (Ts, Te) (step S4), and if it has not been completed, the flow returns to step S3. Thus, the processing of steps S2 and S3 is performed for each measurement time point within the time range (Ts, Te). In this way, at the point in time when the decision in step S4 is Yes, a scale factor waveform representing chronological change in the quantity of target compound present can be obtained. In this scale factor waveform, the scale factor values not at a specific mass-to-charge ratio but rather at the mass-to-charge ratios for which the influence of impurity components is estimated to be the smallest at each measurement time point, as described above, are arranged chronologically. Normally, when scanning measurement is performed on a given compound, multiple peaks will be observed on the mass spectrum, and it is rare for all the peaks to be affected by impurity components. In other words, there is a high likelihood that at least one of the peaks will not be affected by impurity components. Thus, it can be surmised that a scale factor waveform generated as described above will provide a good representation of the shape of the mass chromatogram peaks of the pure target compound.

Next, the quantitation mass selection unit 42 reads, from the measurement data storage unit 5, the measurement data for all measurement time points in the time range (Ts, Te) for mass-to-charge ratio $m_i$ at which a peak is present on the standard mass spectrum of the target compound, and generates a measured mass chromatogram (step S5). The correlation coefficient Con ($m_i$) indicating the correlation of waveform shapes between the measured mass chromatogram peak waveform at this mass-to-charge ratio $m_i$ and the aforementioned scale factor waveform is calculated using the following formula (2) (step S6).

(Mathematical formula 2)

$$\text{Corr}(m_i) = \frac{\sum_{t=t_0}^{T}(F(t)-F')(\text{Int}(m_i,t)-\text{Int}(m_i)')}{\sqrt{\sum_{t=t_0}^{T}(F(t)-F')^2}\sqrt{\sum_{t=t_0}^{T}(\text{Int}(m_i,t)-\text{Int}(m_i)')^2}} \quad (2)$$

In formula (2), F' and Int ($m_i$)' are the mean values of F={F(t)} and Int ($m_i$)={Int ($m_i$, t)} respectively. The flow returns from step S7 to step S5 until the processing of steps S5 and S6 has been carried out for all the mass-to-charge ratios $m_i$, so when the decision in step S7 is Yes, correlation coefficients Corr ($m_i$) will have been obtained for all the mass-to-charge ratios $m_i$.

Figure 3:
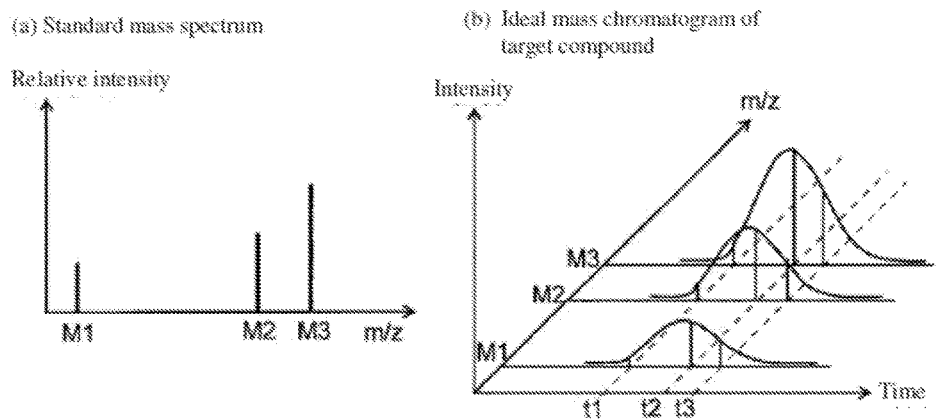
FIG. 3 is a drawing showing an example of embodiment of a standard mass spectrum and ideal mass chromatogram of a target compound.

Here, the significance of the aforesaid correlation coefficient will be explained with reference to FIG. 3 and FIG. 4. If the standard mass spectrum of the target compound is as shown in FIG. 3(a), the ideal mass chromatogram around the retention time of the target compound will be as shown in FIG. 3(b). Namely, mass spectra in a state maintaining the relative ratio of the three peaks at mass-to-charge ratios M1, M2 and M3 appearing in the standard mass spectrum are arranged in the time axis direction (in FIG. 3(b), only t1, t2 and t3 have been shown), and the peak intensities on the mass spectra at each measurement time point for mass-to-charge ratios M1, M2 and M3 are connected in the time axis direction, thereby forming the mass chromatogram peaks. If there is no overlap of impurity components, the shapes of the three mass chromatogram peaks at mass-to-charge ratios M1, M2 and M3 will be similar. Ideally, the aforementioned scale factor waveform will be of a similar shape to the shape of these mass chromatogram peaks.

Figure 4:
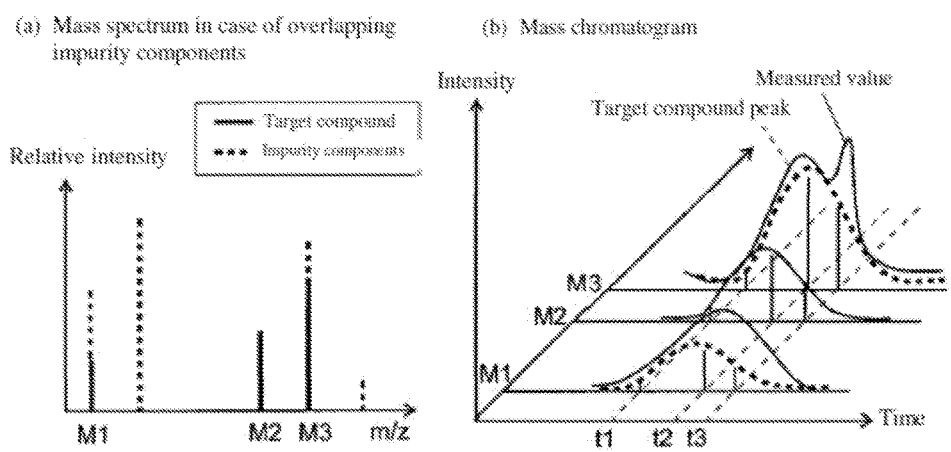
FIG. 4 is a drawing showing an example of a measured mass spectrum and mass chromatogram in a case where impurity components overlap the target compound

An example of a measured mass spectrum and mass chromatogram in the case where some impurity components do overlap the target compound is shown in FIG. 4. As shown in FIG. 4(a), impurity components overlap the peaks at mass-to-charge ratios M1 and M3 derived from the target compound on the mass spectrum, with the peak intensities being increased accordingly. Thus, as shown in FIG. 4(b), in the mass chromatogram in the time range near the retention time of the target compound as well, the shapes of the peaks are altered. In this example, impurity components do not overlap at mass-to-charge ratio M2 at any measurement time point, and the mass chromatogram for mass-to-charge ratio M2 has a peak shape similar to the mass chromatogram of the target compound alone. Therefore, if the correlation coefficients of the scale factor waveform and the mass chromatogram peak waveform at mass-to-charge ratios M1, M2 and M3 are determined, the correlation coefficient between the scale factor waveform and mass chromatogram peak waveform at mass-to-charge ratio M2 should be markedly higher than the others. Conversely, it can be said that a mass-to-charge ratio at which the measured mass chromatogram shows a high correlation coefficient is a mass-to-charge ratio with little influence of impurity components.

The quantitation mass selection unit 42 thus compares the computed n correlation coefficients Corr ($m_i$) to a predetermined threshold T, judges the purity of the measured mass chromatogram peak to be high (little or no overlap of impurity components) for mass-to-charge ratios $m_i$ for which the correlation coefficient Corr ($m_i$) exceeds the threshold T, and extracts such mass-to-charge ratios as quantitation/confirmation mass-to-charge ratio candidates (step S8). The aforementioned threshold T which serves as the criterion can be set to a suitable experimentally determined value. The foregoing is one stage of the selection of quantitation/confirmation mass-to-charge ratios.

Figure 5:
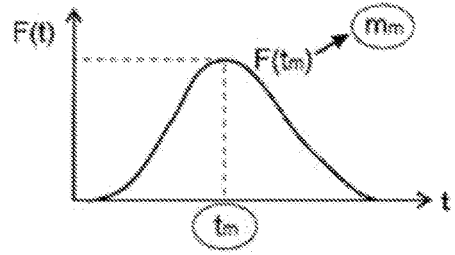
FIG. 5 is an illustration of the method of determination of overlap of impurity components based on peak intensity ratio on a mass spectrum.
Figure 5:
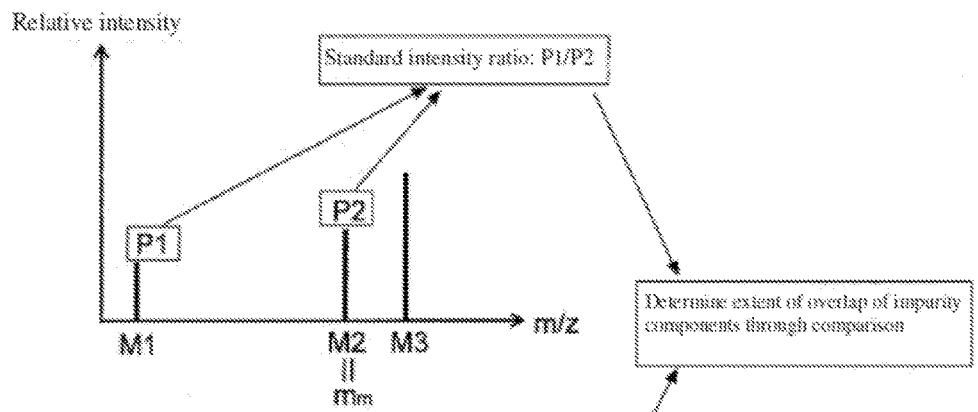
Figure 5:
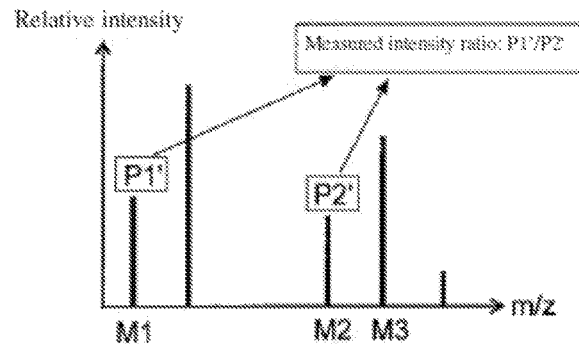

Next, the quantitation mass selection unit 42, using the intensity ratio of mass spectrum peaks contained in the standard mass spectrum of the target compound as reference, determines if the peak intensity ratio on the measure mass spectrum at each measurement time point is within the allowable range, thereby narrowing the mass-to-charge ratios down to mass-to-charge ratios derived solely from the target compound (steps S9 through S11). The specific determination method will be explained with reference to FIG. 5.

First, in the scale factor waveform as shown in FIG. 5(a), it will be assumed that $t_m$ is the time point t at which the scale factor value F (t) is greatest, and that $m_m$ is the mass-to-charge ratio at which the scale factor value F ($t_m$) at that measurement time point $t_m$ was determined. Furthermore, the allowable range A that serves as the criterion is suitably defined. In the measured mass spectrum obtained at measurement time point $t_m$, the mass spectrum peak at mass-to-charge ratio $m_m$ is thought to have the least influence of impurity components. Furthermore, the intensity ratio of the mass spectrum peaks in the standard mass spectrum of the target compound should be maintained in the measured mass spectrum. Thus, as shown in FIG. 5(b), in the standard spectrum of the target compound, the ratio of the peak intensity P2 at mass-to-charge ratio $m_m$ (in this example, M2) and the peak intensity P1 at a different mass-to-charge ratio (in this example, M1) is determined as reference. Then, as shown in FIG. 5(c), on the measured mass spectrum obtained at time point $t_m$, the ratio of the peak intensity P2' at mass-to-charge ratio $m_m$ (in this example, M2) and the peak intensity P1' at another mass-to-charge ratio (in this example, M1) is determined, and it is determined if this intensity ratio falls within the ±A allowable range in relation to the aforementioned reference. To represent this as a formula, this would entail determining whether or not the intensity of the mass spectrum peak at each mass-to-charge ratio $m_i$ satisfies the following formula (3). This is the second stage quantitation/confirmation mass-to-charge ratio selection which follows the above-mentioned first stage.

(Mathematical formula 3)

$$\frac{\text{Int\_std}(m_i)}{\text{Int\_std}(m_m)} - A \leq \frac{\text{Int}(m_i, t_m)}{\text{Int}(m_m, t_m)} \leq \frac{\text{Int\_std}(m_i)}{\text{Int\_std}(m_m)} + A \quad (3)$$

The quantitation mass selection unit 42 determines if the quantitation/confirmation mass-to-charge ratio candidates extracted in step S8 satisfy formula (3), and if formula (3) is satisfied, that mass-to-charge ratio is taken to be a mass-to-charge ratio representing a pure mass chromatogram and is used as a quantitation/confirmation mass-to-charge ratio (step S11). The processing of steps S9 through S11 is performed on all the quantitation/confirmation mass-to-charge ratios extracted in step S8, and when the decision in step S12 is Yes, the quantitation/confirmation mass-to-charge ratios are determined (step S13).

If the quantitation/confirmation mass-to-charge ratios have been determined automatically as described above, the determined quantitation/confirmation mass-to-charge ratios are displayed on the screen of display unit 8. Generally, multiple quantitation/confirmation mass-to-charge ratios are extracted by the processing described above. The analyst checks these on the screen of the display unit 8, and designates the quantitation mass-to-charge ratio and confirmation mass-to-charge ratio to be used for quantitation calculations using the input unit 7. Normally, there will be one quantitation mass-to-charge ratio, but there can be multiple confirmation mass-to-charge ratios.

Receiving this designation, the quantitation computation unit 43, based on measurement data for a standard sample of the target compound at multiple known concentrations stored in advance in the measurement data storage unit 5, generates a mass chromatogram at the designated quantitation mass-to-charge ratio, and generates a calibration curve representing the relationship between the concentration of the target compound and the chromatogram peak area. The quantitation computation unit 43 then computes the area of the measured mass chromatogram peaks at the designated quantitation mass-to-charge ratio, calculates the quantitation value for the target compound by comparing the area value to the aforementioned calibration curve, and displays the quantitation results on the display screen of display unit 8. It is also possible to compute the quantitation value based on measured chromatogram peaks and one or multiple determined quantitation mass-to-charge ratios without any user instruction. In either case, the quantitation calculations are performed based on mass chromatogram peaks with little overlap of impurity components, so a high precision quantitation value is obtained. Furthermore, the quantitation computation unit 43 determines the peak intensities for the designated quantitation mass-to-charge ratio and confirmation mass-to-charge ratio on the mass spectrum during the time of the peak top of the mass chromatogram at the quantitation mass-to-charge ratio, for example, and, from the confirmation ion ratio based thereon, judges if the mass chromatogram peak used for the quantitation computation is derived from the target compound, and outputs the results on the screen of the display unit 8.

Figures 6, 7:
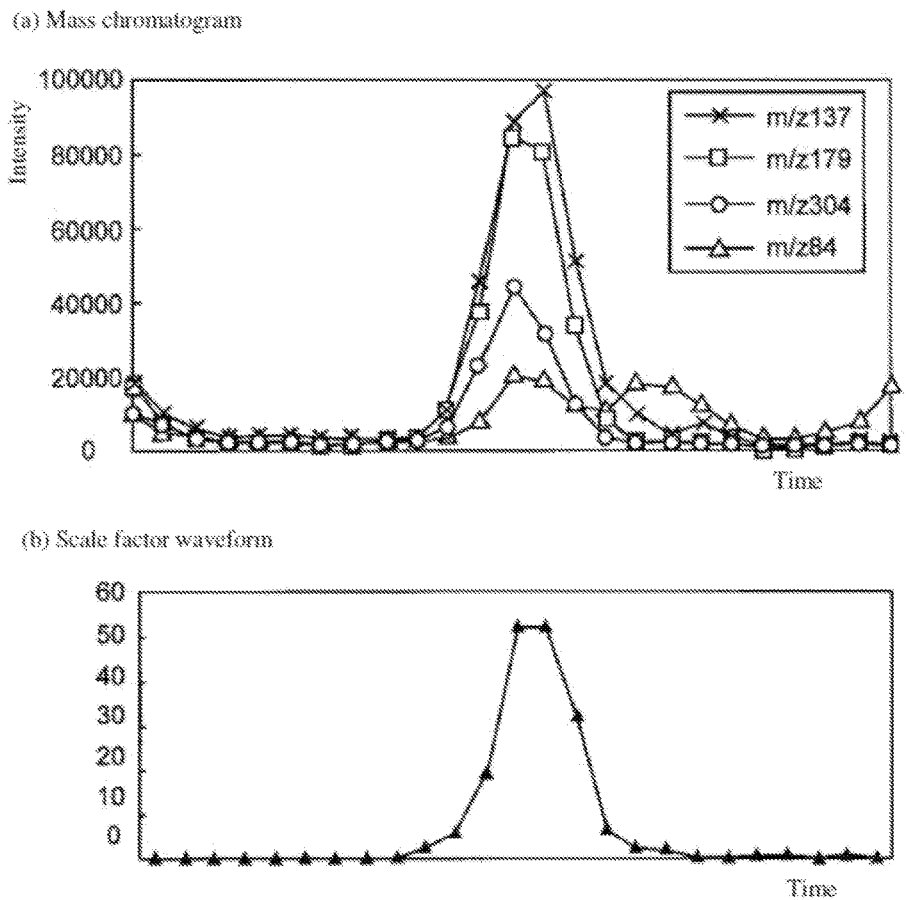
FIG. 6 is a drawing showing a measured mass spectrum obtained for a given target compound and a scale factor waveform computed based thereon.
FIG. 7 is a drawing combining the correlation coefficients, peak intensity ratios, etc., calculated based on FIG. 6.

An actual example of the data processing described above will be explained using FIG. 6 and FIG. 7. FIG. 6(a) shows mass chromatograms at m/z 137, m/z 179, m/z 304 and m/z 84 obtained for a given target compound. Furthermore, FIG. 6(b) is a scale factor waveform determined based on the standard mass spectrum of the target compound and measured mass spectrum data by the method described above. This scale factor waveform has a shape close to normal distribution. FIG. 7 is a drawing combining the results of computation of correlation coefficients, etc. based on the measured mass chromatograms shown in FIG. 6(a) and the scale factor waveform shown in FIG. 6(b).

As can be seen from FIG. 7, the mass chromatograms for m/z 137, m/z 179 and m/z 304 all show a good correlation coefficient of over 0.9. On the other hand, for m/z 84, the correlation coefficient has a low value due to the presence of impurity components. As a result, based on the first stage determination, m/z 137, m/z 179 and m/z 304 are included as quantitation/confirmation mass-to-charge ratio candidates, while m/z 84 is excluded.

The quantitation/confirmation mass-to-charge ratio candidates are narrowed down further on the basis of intensity ratio of mass spectrum peaks on the standard mass spectrum. The m/z given the greatest scale factor in the scale factor waveform shown in FIG. 6(b) was 137, in which case, in the measured mass spectrum at measurement time point t showing the greatest scale factor, the mass spectrum peak intensity at m/z 137 is thought to have the least influence of impurity components. Thus, the ratio (Int_std ($m_i$)/Int_std (137)) of the mass spectrum peak intensity of each mass-to-charge ratio candidate to the peak intensity of m/z 137 in the standard mass spectrum of the target compound and the ratio (Int($m_i$)/Int (137)) of the mass spectrum peak intensity of each mass-to-charge ratio candidate to the peak intensity of m/z 137 in the measured mass spectrum at measurement time point t are compared. If the allowable range A was set to 20, it can be seen that m/z 304 has produced a difference which exceeds the allowable range. This indicates the possibility that other components besides the target compound were eluted at the same time. In light of these results, m/z 304 is excluded from among the quantitation/confirmation mass-to-charge ratio candidates. Consequently, in this example, the two ratios m/z 137 and m/z 179 are determined as the quantitation/confirmation mass-to-charge ratios.

It should be noted that the example of embodiment described above is an example of the present invention, and suitable modifications, alterations and additions made within the gist of the present invention are obviously included within the scope of patent claims of the present application.

For example, in the example of embodiment described above, the scale factor waveform generated in steps S2 through S4 can also be generated through another procedure. Namely, it is possible to multiply the intensities of each peak on the standard mass spectrum by a constant scaling factor such that they do not exceed the measured peak intensities for the multiple mass-to-charge ratios on the standard mass spectrum of the target compound, and find a chromatogram peak waveform of the target compound alone which is not affected by overlap of impurity components when that scale factor is determined at each measurement time point, in the same way as in formula (1).

Furthermore, in the foregoing example of embodiment, the invention was applied to a GC/MS, but obviously the invention can also be applied to an LC/MS.

DESCRIPTION OF REFERENCES

1 . . . Gas chromatograph section (GC section)
10 . . . Sample gasification chamber
11 . . . Injector
12 . . . Column
13 . . . Column oven
2 . . . Mass spectrometry section (MS section)
20 . . . Ion source
21 . . . Quadrupole mass filter
22 . . . Ion detector
3 . . . A/D converter
4 . . . Data processing unit
41 . . . Data collection unit
42" . . . Quantitation mass selection unit
43 . . . Quantitation computation unit
5 . . . Measured data storage unit
6 . . . Compound database (DB)
7 . . . Input unit
8 . . . Display unit

What is claimed is:

1. A chromatography/mass spectrometry data processing system which analyzes and processes data including mass-to-charge ratios, time, and signal intensities, wherein the chromatography/mass spectrometry data processing system is configured to repeatedly execute mass analysis across a predetermined mass-to-charge ratio range after separating components in a sample with a chromatograph, the chromatography/mass spectrometry data processing system comprising:
   a chromatograph configured to separate sample components;
   a mass spectrometer configured to ionize the sample components and sort ions according to mass-to-charge ratios; and
   a processor, wherein the processor includes:
      a) a chromatogram peak shape estimation unit which, using a plurality of intensity ratios, wherein each intensity ratio comprises:
         an intensity of a peak on a standard mass spectrum of a target compound, which is an object of analysis, and
         an intensity of peaks having a same mass-to-charge ratio on a measured mass spectrum at various measurement time points near a retention time of said target compound,
      estimates shapes of chromatogram peaks due to said target compound from which an influence of overlap of impurity components has been eliminated, based on a minimum value of one of the plurality of intensity ratios;
      b) a chromatogram peak correlation determination unit which determines a correlation between the shapes of the chromatogram peaks obtained by said chromatogram peak shape estimation unit and peaks of said target compound on a measured mass chromatogram obtained at each mass-to-charge ratio;
      c) a mass spectrum peak purity determination unit which determines mass spectrum peaks originating solely from the target compound based on:
         an intensity ratio of multiple peaks on the standard mass spectrum of said target compound, and
         an intensity ratio of multiple peaks having the same mass-to-charge ratio on the measured mass spectrum of the target compound at a specific measurement time point; and
      d) a mass-to-charge ratio derivation unit which, using determination results of said chromatogram peak correlation determination unit and determination results of said mass spectrum peak purity determination unit, derives a mass-to-charge ratio as a confirmation mass-to-charge ratio and/or quantitation mass-to-charge ratio used for quantitating said target compound.

2. The chromatography/mass spectrometry data processing system as described in claim 1,
   wherein said chromatogram peak shape estimation unit determines an intensity ratio Ps/Pr, wherein Ps comprises peak intensity on the measured mass spectrum, and Pr comprises peak intensity on the standard mass spectrum, of peaks having the same mass-to-charge ratio on the measured mass spectrum at a given measurement time point for the mass-to-charge ratio of all or some of the peaks on the standard mass spectrum of said target compound,
   wherein said chromatogram peak shape estimation unit takes a smallest intensity ratio Ps/Pr of multiple intensity ratios Ps/Pr as a scale factor at that measurement time point, and arranges scale factors determined at each measurement time point in a time series order to estimate shapes of the chromatogram peak of said target compound.

3. The chromatography/mass spectrometry data processing system as described in claim 2,
   wherein said mass spectrum peak purity determination unit determines a reference measurement time point and a reference mass-to-charge ratio which indicates the peak top of the chromatogram peak obtained by said chromatogram peak shape estimation unit, and taking as reference the ratio of the peak intensity for the reference mass-to-charge ratio on the standard mass spectrum of said target compound to the peak intensity at an arbitrary mass-to charge ratio, determines if the ratio of peak intensity for the reference mass-to-charge ratio on the measured mass spectrum at said reference measurement time point to the peak intensity at said arbitrary mass-to-charge ratio falls within a predetermined range in relation to said reference, and determines if the peak for the arbitrary mass-to-charge ratio is a mass spectrum peak originating solely from said target compound.

4. The chromatography/mass spectrometry data processing system as described in claim 1,
   wherein when the intensity of all or some of the peaks on the standard mass spectrum of said target compound is multiplied by a constant scaling factor and compared to the intensity of the peak having the same mass-to-charge ratio on the measured mass spectrum at a given measurement time point, said chromatogram peak shape estimation unit determines a constant scale factor, such that a former intensity does not exceed a latter intensity, and arranges the scale factors determined at each measurement time point in a time series order to estimate shapes of the chromatogram peaks of said target compound.

5. The chromatography/mass spectrometry data processing system as described in claim 4,
   wherein said mass spectrum peak purity determination unit determines a reference measurement time point and a reference mass-to-charge ratio which indicate the peak top of the chromatogram peak obtained by said chromatogram peak shape estimation unit, and taking as reference the ratio of the peak intensity for the same reference mass-to-charge ratio on the standard mass spectrum of said target compound to the peak intensity at an arbitrary mass-to charge ratio, determines if the ratio of peak intensity for the reference mass-to-charge ratio on the measured mass spectrum at said reference measurement time point to the peak intensity at said arbitrary mass-to-charge ratio falls within a predetermined range in relation to said reference, and determines if the peak for the arbitrary mass-to-charge ratio is a mass spectrum peak originating solely from said target compound.

6. The chromatography/mass spectrometry data processing system as described in claim 1,
   wherein said mass spectrum peak purity determination unit determines a reference measurement time point and a reference mass-to-charge ratio indicates the peak top of the chromatogram peak obtained by said chromatogram peak shape estimation unit, and taking as reference the ratio of the peak intensity for the reference mass-to-charge ratio on the standard mass spectrum of said target compound to the peak intensity at an arbitrary mass-to charge ratio, determines if the ratio of peak intensity for the reference mass-to-charge ratio on the measured mass spectrum at said reference measurement time point to the peak intensity at said arbitrary mass-to-charge ratio falls within a predetermined range in relation to said reference, and determines if the peak for the arbitrary mass-to-charge ratio is a mass spectrum peak originating solely from said target compound.

7. The chromatography/mass spectrometry data processing system as described in claim 1, further comprising a display for displaying the confirmation mass-to-charge ratio and/or quantitation mass-to-charge ratio used for quantitating said target compound.

8. A chromatography/mass spectrometry data processing method in which data including mass-to-charge ratios, time, and signal intensities are obtained by repeatedly executing mass analysis across a predetermined mass-to-charge ratio range after separating components in a sample with a chromatograph, the chromatography/mass spectrometry data method comprising:
   separating sample components with a chromatograph;
   ionizing the sample components and sorting ions according to mass-to-charge ratios with a mass spectrometer;
   a) using a plurality of intensity ratios, wherein each intensity ratio comprises:
      an intensity of a peak on a standard mass spectrum of a target compound which is an object of analysis, and
      an intensity of peaks having a same mass-to-charge ratio on a measured mass spectrum at various measurement time points near a retention time of said target compound,
   estimating, with a processor, shapes of chromatogram peaks due to said target compound from which an influence of overlap of impurity components has been eliminated, based on a minimum value of one of the plurality of intensity ratios;
   b) determining, with the processor, a correlation between the shapes of the obtained chromatogram peaks and peaks of said target compound on a measured mass chromatogram obtained at each mass-to-charge ratio;
   c) determining, with the processor, mass spectrum peaks originating solely from the target compound based on:
      an intensity ratio of multiple peaks on the standard mass spectrum of said target compound, and:
      an intensity ratio of multiple peaks having the same mass-to-charge ratio on the measured mass spectrum of the target compound at a specific measurement time point;
   d) using chromatogram peak correlation determination results and mass spectrum peak purity determination results, deriving, with the processor, a mass-to-charge ratio as a confirmation mass-to charge ratio and/or quantitation mass-to-charge ratio used for quantitating said target compound.

9. The chromatography/mass spectrometry data processing method as described in claim 8, further comprising displaying the confirmation mass-to-charge ratio and/or quantitation mass-to-charge ratio used for quantitating said target compound on a display.

10. A chromatography/mass spectrometry data processing system which analyzes and processes data including mass-to-charge ratios, time, and signal intensities, and is configured to repeatedly execute mass analysis across a predetermined mass-to-charge ratio range after separating components in a sample with a chromatograph,
   wherein the chromatography/mass spectrometry data processing system comprises:

a chromatograph configured to separate sample components;

a mass spectrometer configured to ionize the sample components and sort ions according to mass-to-charge ratios; and a processor configured to:
  a) using a plurality of intensity ratios, wherein each intensity ratio comprises:
    an intensity of a peak on a standard mass spectrum of a target compound which is an object of analysis, and
    an intensity of peaks having a same mass-to-charge ratio on a measured mass spectrum at various measurement time points near a retention time of said target compound,
  estimate shapes of chromatogram peaks due to said target compound from which an influence of overlap of impurity components has been eliminated, based on a minimum value of one of the plurality of intensity ratios;
  b) determine a correlation between the shapes of the chromatogram peaks obtained by the processor and peaks of said target compound on a measured mass chromatogram obtained at each mass-to-charge ratio;
  c) determine mass spectrum peak purity by determining mass spectrum peaks originating solely from the target compound based on:
    an intensity ratio of multiple peaks on the standard mass spectrum of said target compound, and
    an intensity ratio of multiple peaks having the same mass-to-charge ratio on the measured mass spectrum of the target compound at a specific measurement time point; and
  d) using the correlation and the mass spectrum peak purity, derive a mass-to-charge ratio as a confirmation mass-to-charge ratio and/or quantitation mass-to-charge ratio used for quantitating said target compound.

11. The chromatography/mass spectrometry data processing system as described in claim 10, further comprising a display for displaying the confirmation mass-to-charge ratio and/or quantitation mass-to-charge ratio used for quantitating said target compound.

* * * * *